United States Patent
Verhagen

(10) Patent No.: US 9,897,800 B2
(45) Date of Patent: Feb. 20, 2018

(54) LASER SCANNING SYSTEM, HAIR-CUTTING DEVICE AND CORRESPONDING METHOD

(75) Inventor: Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1170 days.

(21) Appl. No.: 13/637,112

(22) PCT Filed: Mar. 29, 2011

(86) PCT No.: PCT/IB2011/051327
§ 371 (c)(1),
(2), (4) Date: Sep. 25, 2012

(87) PCT Pub. No.: WO2011/121536
PCT Pub. Date: Oct. 6, 2011

(65) Prior Publication Data
US 2013/0018362 A1    Jan. 17, 2013

(30) Foreign Application Priority Data
Apr. 1, 2010 (EP) ..................... 10158930

(51) Int. Cl.
*A61B 18/18* (2006.01)
*G02B 26/10* (2006.01)
(Continued)

(52) U.S. Cl.
CPC ............ *G02B 26/10* (2013.01); *A61B 18/203* (2013.01); *G02B 26/0816* (2013.01);
(Continued)

(58) Field of Classification Search
CPC ........ A61B 2018/00476; A61B 18/203; A61B 2018/202; A61B 2018/20359; A61B 2018/00452; G02B 26/10; G02B 26/0816
See application file for complete search history.

(56) References Cited

U.S. PATENT DOCUMENTS 3,972,583 A * 8/1976 Lobb ........................ H04N 3/08
348/203
5,764,398 A   6/1998 Hayakawa
(Continued)

FOREIGN PATENT DOCUMENTS

JP    2007171854 A    7/2007
WO   WO2005011510 A1   2/2005
(Continued)

*Primary Examiner* — Lindsey G Wehrheim

(57) ABSTRACT

A laser scanning system for scanning a laser beam of a hair cutting device includes a laser scanning device for generating a scanning movement of the laser beam and a movable optical device for adjusting and/or focusing the laser beam. The laser scanning device includes an arrangement with at least one movable optical element which is mechanically coupled to the movable optical device, and an optical system fixed to the laser scanning device. The movable optical element is arranged to inter-relate a position of the movable optical device to a mobile access-position where the laser beam enters the optical system. Further, the optical system is arranged to inter-relate said mobile access-position to at least one corresponding position where the laser beam is incident on the movable optical device.

19 Claims, 3 Drawing Sheets

(51) Int. Cl.
  *G02B 26/08*  (2006.01)
  *A61B 18/20*  (2006.01)
  *A61B 18/00*  (2006.01)

(52) U.S. Cl.
  CPC .............. *A61B 2018/00452* (2013.01); *A61B 2018/00476* (2013.01); *A61B 2018/202* (2013.01); *A61B 2018/20359* (2017.05)

(56) References Cited

U.S. PATENT DOCUMENTS

| | | |
|---|---|---|
| 6,445,944 B1 | 9/2002 | Ostrovsky |
| 7,101,365 B1 | 9/2006 | Sharon |
| 7,108,690 B1 | 9/2006 | Lefki |
| 2002/0013577 A1 | 1/2002 | Frey et al. |
| 2003/0223077 A1* | 12/2003 | Hill ................... G03F 7/70775 356/498 |
| 2006/0200116 A1* | 9/2006 | Ferren ................. A61B 18/203 606/9 |

FOREIGN PATENT DOCUMENTS

| | | |
|---|---|---|
| WO | WO2007013008 A1 | 2/2007 |
| WO | WO2008120141 A2 | 10/2008 |

* cited by examiner

LASER SCANNING SYSTEM, HAIR-CUTTING DEVICE AND CORRESPONDING METHOD

FIELD OF THE INVENTION

The invention relates to the field of a laser scanning system adapted for scanning a laser beam of a hair cutting device, the laser scanning system comprising a laser scanning device for generating a scanning movement of the laser beam and a movable optical device for adjusting and/or focussing the laser beam. The invention further relates to a corresponding hair-cutting device (a laser shaver) and a corresponding method of scanning a laser beam by means of a laser scanning device for generating a scanning movement of the laser beam and a movable optical device for adjusting and/or focussing the laser beam.

BACKGROUND OF THE INVENTION

A laser scanning system for scanning a laser beam of a hair cutting device comprises a moving optical device like e.g. a vibrating array of optical means to direct a number of focal spots in a harmonic motion over the skin of an individual. Said vibrating motion of the array ensures that every point covered by a detection device has been examined for the presence of hairs and/or has, potentially, been shaved by guiding high power optical pulses to each detected hair.

Document WO 2007/013008 A1 describes a hair-removing system comprising a hair-detection device and a hair-removing device that is operatively coupled to the hair-detection device as well as an image sensor to detect an image of a part of the skin to be treated, wherein the image sensor comprises a moving array of lenses.

Because of the vibratory motion of the optical means, in most designs a tracking mechanism is employed to ensure a continuous overlap or allignment of the laser beam with the movable optical device. This tracking mechanism could consist e.g. of an electro-optical or acousto-optical deflector, a vibrating tracking mirror or tracking prism, a liquid crystal beam deflector, etc. The tracking mechanism needs to be accurately synchronized with respect to the phase, amplitude, and actual resonance frequency of the movable optical device and its associated mechanics and actuators. Furthermore, the tracking mechanism needs to be fast enough to track the motion of the movable optical device and be able to handle the detection laser light and preferably also the high power cutting laser light and be generally compatible with the overall requirements for laser shaving (i.e. low cost, low voltage, small in size, low power consumption, etc.). This set of requirements is difficult to meet using the solutions mentioned above. Furthermore, the solutions should also work in many ambient conditions (temperature, pressure, moisture) and be reasonably shock resistant and very reliable.

SUMMARY OF THE INVENTION

It is an object of the invention to provide a laser scanning system for a hair cutting device, the corresponding hair cutting device and a method of scanning a laser beam enabling precise tracking of the movable optical device's trace with the laser light.

The present invention aims to overcome the tracking difficulties by making the laser scanning system self-tracking, i.e. the motion of the movable optical device itself ensures that the appropriate overlap or allignment between the movable optical device and the incident laser beam (detection laser beam and/or cutting laser beam) is always obtained.

The laser scanning device of the laser scanning system according to the invention comprises an arrangement with at least one movable optical element which is mechanically coupled to the movable optical device and an optical system which is fixed to the laser scanning device, wherein the movable optical element is arranged to inter-relate a position of the movable optical device to a mobile access-position where the laser beam enters the optical system, and wherein the optical system is arranged to inter-relate said mobile access-position to at least one corresponding position where the laser beam is incident on the movable optical device. This position is a fixed position at the movable optical device. The synchronized movement of the movable optical element with respect to the movement of the movable optical device allows both simple and precise tracking of the motion of the movable optical device by the laser beam.

According to a preferred embodiment of the invention, the movable optical element and the movable optical device are fixed to one another, especially directly fixed to one another.

According to another preferred embodiment of the invention, the movable optical element is a reflective element adjusted for reflecting the laser beam in a direction parallel to a moving axis of the movable optical element and the movable optical device.

According to yet another preferred embodiment of the invention, the reflective element is arranged in a 45-degree (45°) orientation with respect to an incoming direction and with respect to an outgoing direction of the laser beam. The reflective element preferably is a single reflective 45-degree mirror directly mounted on the movable optical device. The mirror is positioned such that the light incident on this mirror undergoes, apart from a 90-degree change in a direction parallel to the direction of movement of the movable optical device, also a lateral displacement perpendicular to the direction of movement of the movable optical device. The magnitude of this displacement depends on the actual phase of the movable optical device relative to the incident laser beam.

According to another preferred embodiment of the invention, the movable optical device comprises an array of optical means for adjusting and/or focussing the laser beam. The array of optical means preferably is a linear array of conical mirrors to create a number of adjacent focus points. The position where the laser beam is incident on the movable optical device preferably is a position at one of the optical means.

According to another preferred embodiment of the invention, the mobile access position where the laser beam enters the optical system fixed to the laser scanning device is a position on a first reflective means of the optical system. The first reflective means especially is a 45° (45-degree) reflective means positioned somewhere on the non-moving part of the laser scanning system like e.g. a housing or a frame, such that the laser beam, after being deflected by the movable reflective element (mirror) in a 45-degree orientation, strikes the fixed 45-degree reflective means. The reflecting surfaces of the movable reflective element and the fixed first reflective means are positioned parallel to one another such that the direction of propagation of the laser light before and after the double reflection is the same. In this way, the lateral movement of the laser beam is properly maintained.

According to yet another preferred embodiment of the invention, the optical system further comprises a second reflective means and a third reflective means, wherein each of the first, second and third reflective means is arranged in a 45° orientation with respect to an incoming direction and with respect to an outgoing direction of the laser beam.

Using the appropriate reflective optics to redirect the laser beam, one can ensure that the lateral beam displacement coincides with the motion of the movable optical device, especially in the case that the movable optical device comprises an array of optical means, thereby making the movable optical device self tracking. It is essential that the movable reflective element arranged in 45-degree (45°) orientation is positioned close to the movable optical device such that the amplitude, frequency, and phase of the movement are the same as those of the movable optical device. In this way, all phase, frequency, and amplitude variations due to manufacturing tolerances, temperature, pressure, ageing, etc. will automatically be compensated without additional need for advanced readout and feedback control systems and advanced beam deflection systems to ensure tracking under all conditions.

According to another preferred embodiment of the invention, at least one of the first, second and third reflective means is part of a faceted prism for selectable addressing the individual optical means of the array by changing the position of the prism.

According to another preferred embodiment of the invention, the optical system further comprises at least one focussing element. The focusing element is a lens, especially a cylindrical lens arranged in the optical path of the laser beam between the first and the second reflective means of the optical system.

The hair cutting device according to the invention comprises the aforementioned laser scanning system, a detection system for detecting hair with a laser device, and/or a cutting-laser system with a cutting-laser device.

According to a preferred embodiment of the invention, the detection system and/or the cutting-laser system use a common optical path of the hair cutting device. The laser beam of the detection system and/or the cutting-laser system use the common optical path to impact the movable optical element.

According to another preferred embodiment of the invention, the detection system comprises a beam-splitting device arranged in the common optical path, which beam-splitting device is optically connected to the laser device by a first optical path and is optically connected to a detection device by a second optical path.

According to another preferred embodiment of the invention, the detection device comprises a focussing system, a pin hole and a detector arranged in the second optical path.

According to another preferred embodiment of the invention, the cutting-laser system comprises a further beam-splitting device arranged in the common optical path, which further beam-splitting device is connected to a cutting-laser device by a further optical path.

A method of scanning a laser beam according to the invention uses a laser scanning device comprising an arrangement with a fixed optical system and with at least one moving optical element which is mechanically coupled to the movable optical device, wherein the movable optical element inter-relates a position of the movable optical device to a mobile access-position where the laser beam enters the fixed optical system, and the fixed optical system inter-relates said access-position of the laser beam to at least one corresponding position of the movable optical device.

Preferably, the movable optical element and the movable optical device are fixed to one another, especially directly fixed to one another. Especially the movable optical element is a reflective element adjusted for reflecting the laser beam in a direction parallel to a moving axis of the movable optical element and the movable optical device.

According to a preferred embodiment of the invention, the reflective element is arranged in a 45-degree (45°) orientation with respect to an incoming direction and with respect to an outgoing direction of the laser beam. The reflective element preferably is a single reflective 45-degree mirror directly mounted on the movable optical device. The mirror is positioned such that the light incident on this mirror undergoes, apart from a 90-degree change of direction parallel to the direction of movement of the movable optical device, also a lateral displacement perpendicular to the direction of movement of the movable optical device. The magnitude of this displacement depends on the actual phase of the movable optical device relative to the incident laser beam.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
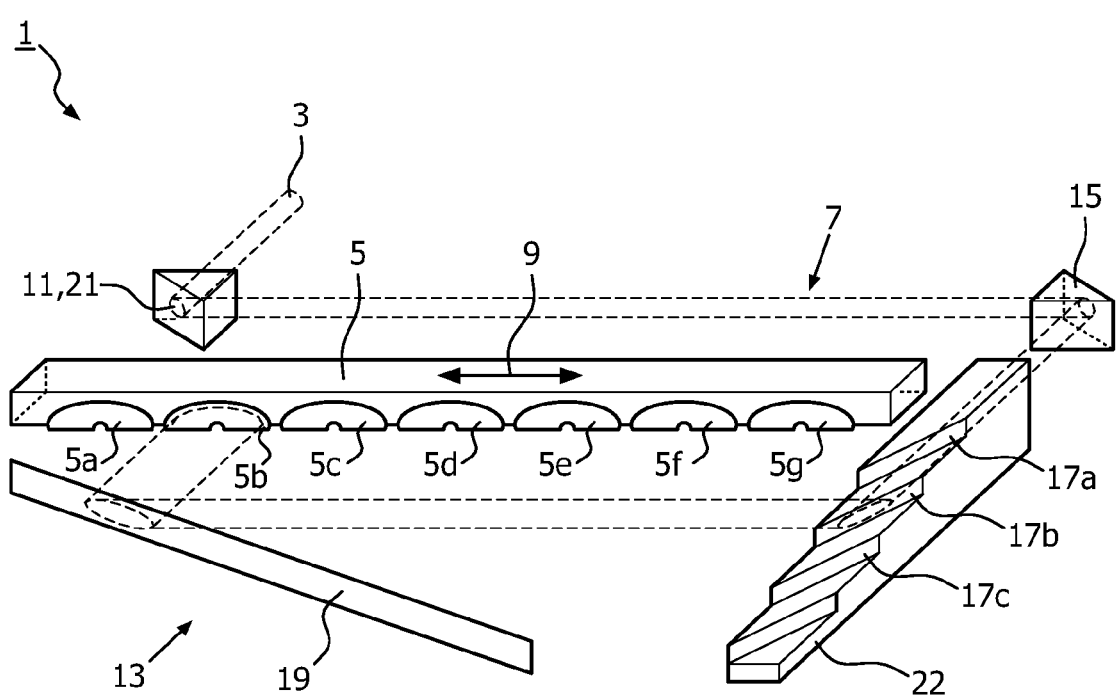
FIG. 1 schematically shows a laser scanning system for scanning a laser beam of a hair cutting device according to a preferred embodiment of the invention.

FIG. 1 illustrates a laser-scanning system 1 for scanning a laser beam 3 of a hair cutting device. The laser beam 3 can be a laser beam of a high power cutting laser device or a laser beam of a laser device of a detection system. The laser-scanning system 1 comprises two main assemblies: a movable optical device 5 for adjusting and/or focussing the outgoing scanning laser beam and a laser scanning device 7 for generating the scanning movement of the scanning laser beam. The movement of the optical device 5 preferably is a vibration movement, which movement is indicated by a double arrow 9.

The movable optical device 5 shown in FIG. 1 comprises a linear array of optical means 5a, 5b, 5c, 5d, 5e, 5f, 5g for adjusting and/or focussing the outgoing scanning laser beam. Said optical means are conical mirrors to create a number of adjacent focus points.

The scanning device 7 comprises an arrangement with a movable optical element 11, mechanically coupled to the movable optical device 5, and an optical system 13 comprising three reflective means 15, 17, 19 fixed in the laser-scanning device. The optical element 11 is a reflective element 21 arranged to interrelate the position of the movable optical device 5 to a mobile access-position 23 on the first reflective means 15. Each of the reflective element 21 and the reflective means 15, 17, 19 is arranged in a 45° orientation with respect to the incoming and outgoing laser beam 3. Further, the optical system 13 is arranged to inter-relate said mobile access-position to a corresponding position where the scanning laser beam strikes the movable optical device 5. The movable optical element 11 and the movable optical device 5 are directly fixed to one another for synchronization of the movement of the movable optical device 5 and the incidence of the scanning laser beam.

Each of the reflective element 21 and the first reflective means 15 is formed as a prism, the second reflective means 17 is formed as a faceted prism 22 for selectable addressing the individual optical means 5a, 5b, 5c, 5d, 5e, 5f, 5g of the array via the third reflective means 19, which third reflective means 19 is formed as a tilted mirror. The three reflective means are enumerated in the direction of laser light propagation. An additional focussing element 25, a cylindrical lens, is located in the optical path of the laser beam between the first and the second reflective means 15, 17.

The optical device 5 comprises the array of optical means being conical mirrors, in which the mirror aperture is typically 0.4×1.7 mm while the pitch between the optical means (the mirrors) could vary from 1.7 mm to very large interspaces. The conical mirror array vibrates in a leaf spring system (not shown) with a certain resonance frequency, relative phase, and amplitude. The direction of the vibration is indicated in the picture by the double headed arrow 9. The amplitude is sufficient such that the movement of the focus of the conical mirrors ensures that an entire surface is scanned during one half-period of the vibration. The optical element 11 (being a mirror or a prism) is attached, or mechanically connected, to the conical mirror array, such that it precisely follows the motion of the array under all operating conditions. The laser beam 3 is perpendicularly incident on the scanning motion (double arrow 9) of the reflective element 21 and optical device 5 and is deflected to become essentially parallel to the scanning motion and is collected by the first reflective means 15 (aligned as a 45 deg mirror) which is fixed to the same frame as the light source itself (i.e. is not moving with the optical device vibration). Depending on the vertical angle of incidence of the light on reflective element 21, the light will impinge on one of the mirror surfaces of the complex optical prism forming the second reflective means 17 and be deflected to a 45 degree tilted third reflective means 19 such that the laser beam is deflected towards the entrance of one of the optical means (namely the conical mirrors) 5a, . . . , 5g in the array.

Alternatively, laser light may be incident on all reflecting surfaces of the second reflective means 17 simultaneously, allowing simultaneous illumination of all optical means (conical mirrors) 5a, . . . , 5g of the array.

Cylindrical optics may be employed between the reflective element 21 and the first reflective means 15 or between the first and second reflective means 15, 17 to collimate and parallelize the laser beam(s) and reduce the complexity of the second reflective means 17. Additionally the reflective means 15, 17, 19 may be constructed from a single piece of optical material, i.e. glass, thereby ruggedizing the overall system in terms of maintaining optical alignment under all kinds of harsh conditions.

Figure 2:
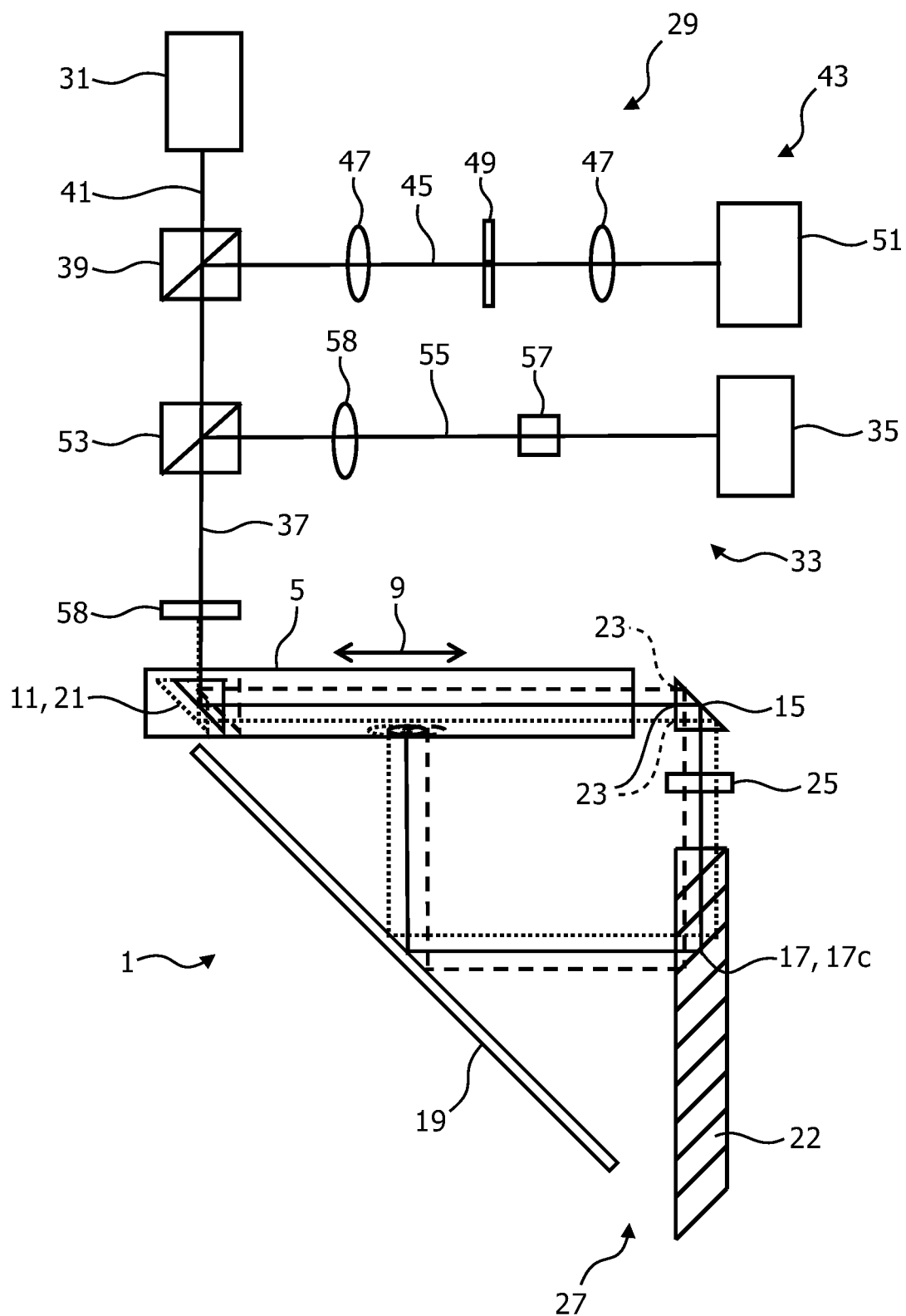
FIG. 2 schematically shows a hair cutting device comprising the laser scanning system of FIG. 1, a detection system and a cutting laser system.

The effect of the 3D arrangement of optical parts as described above will be described referencing to the 2D layout of the components as schematically depicted in FIG. 2. The laser beams will be designated by the chief rays only.

In FIG. 2 the chief ray of the laser beam 3 is depicted as it is traced through the scanning system 1 in the centre, left, and extreme right mechanical position of the conical mirror array 5a, . . . , 5g by the drawn, dotted, and dashed line, respectively. It is clear that the laser beam 3 as indicated in the picture tracks one conical mirror (indicated by the drawn, dotted, and dashed ellipses) irrespective of the actual position of the optical device 5 with the conical mirror array. Additionally, it is clear that by changing slightly the angle or height of the laser beam 3 to a position out of the plane of the paper, it is possible to randomly select one of the reflective surfaces 17a, 17b, 17c, 17d, 17e, 17f, 17g of the prism 22 in order to address one specific conical mirror. Furthermore, by illuminating all reflecting surfaces of prism 22 it is possible to illuminate all conical mirrors while maintaining the tracking behaviour of the system 1. That is to say, the illuminating beam will be distributed over all conical mirrors 5a, . . . , 5g (or other individual optical means), wherein one part of the cross-section of the beam will be addressing the same conical mirror/optical means independent of the actual phase within the vibration period of the conical mirror array. An added benefit of the current layout is that, in order to address a single optical means (conical mirror), the amount of laser beam deflection required is proportional to the small axis of the optical means/conical mirror. When, instead, a single addressing mirror is used to address the conical mirrors directly, the total pitch between two conical mirrors would be the determining factor for the required beam deflection, which can easily be 5 to 10 times larger.

FIG. 2 shows a corresponding hair cutting device 27, comprising the laser scanning system 1 according to FIG. 1 and a detection system 29 with a laser device 31 for detecting hair and a cutting laser system 33 with a cutting laser device 35. The detection system 29 and/or a cutting laser system 33 uses a common optical path 37 of the hair cutting device 27.

The detection system 29 comprises a beam splitting device 39 arranged in the common optical path 37, which beam splitting device 39 is connected to the laser device 31 by a first optical path 41, and a detection device 43 in a second optical path 45. The detection device 43 comprises a focussing system 47, a pin hole 49, and a detector 51 arranged in the second optical path 45. The cutting laser system 33 comprises a further beam splitting device 53 arranged in the common optical path 37, which further beam splitting device 53 is connected to the cutting laser device 35 by a further optical path 55.

Figure 3:
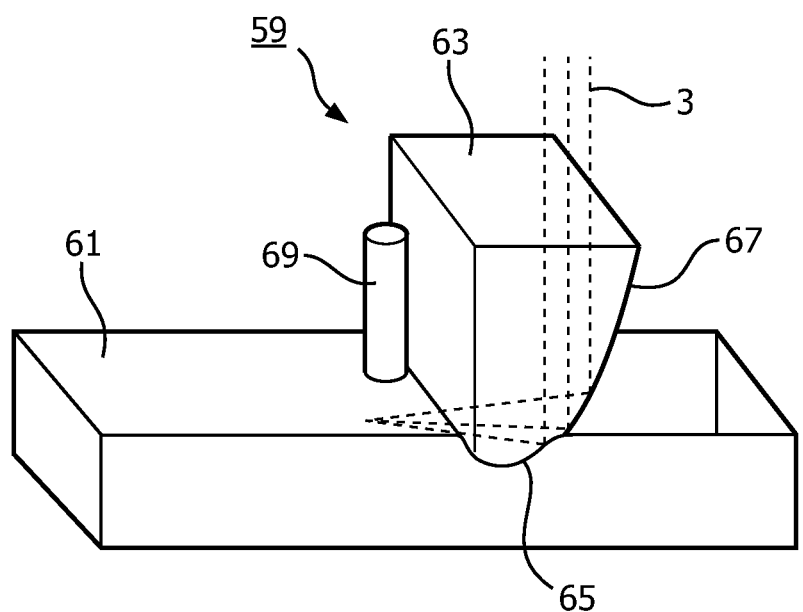
FIG. 3 illustrates the internal reflection to deflect and focus an incident light beam to a point outside an optical blade being in contact with skin and hair.

FIGS. 2 and 3 show how an optical blade 59 incorporating the laser scanning system 1 can be integrated with a parallel detection system and with the addressing and hair cutting device 27.

The cutting laser device 35 is focused on a deflection means 57 (i.e. a rotatable prism/mirror, a liquid crystal waveguide, an electro-optical deflector, or the like) such that it is deflected out of the plane of the paper, allowing it to be made incident on only one of facets 17a, . . . , 17g of the faceted prism 22 and hence be guided on only one of the optical means (conical mirror elements). At the same time, the detection laser device 31 can be arranged such that the laser beam is incident on all facets 17a, . . . , 17g simultaneously (by using a larger beam diameter). Hence, the light returning from each of the facets 17a, . . . , 17g represents the signal emanating from one of the conical mirror elements 5a, . . . , 5g. A combination of lenses 58 and pinholes can be used to ensure confocal detection, i.e. to ensure that, when the light of the conical mirror array 5a, . . . , 5g is detected by using an array of photodetectors forming the detector 51, each single element of the detector array receives only light emanating from the focus of the corresponding conical mirror element and out-of-focus light is efficiently rejected.

FIG. 3 shows an optical blade 59 with internal reflection to deflect and focus the incident light, indicated as drawn lines, to a point outside the optical blade 59, such that the central direction of the light becomes parallel to a surface, such as the skin surface 61. The optical blade 59 comprises a blade body 63 and a tapered end 65, wherein the tapered end 65 comprises a parabolic reflector 67.

FIG. 3 further shows the optical blade brought into contact with skin and hair 69 according to a second preferred embodiment of the invention. The optical blade 59 indents the skin surface 61, thereby preferably providing access to the hair 69 at a level below the skin surface 61, enabling the hair 69 to be cut at a level that was originally below skin surface 61. According to a preferred embodiment of the invention, an opportunity to detect the presence of a hair 69 at the focus position of the optical blade 59 is provided. Further, an active hair manipulation means is preferably used to manipulate or retract the hair 69 to achieve an even closer shave. Therefore, serrated blade geometries are preferably used.

Once the hair 69 is cut and the skin surface 61 again relaxes from the imposed strain, i.e. the optical blade 59 is removed, the hair 69 has preferably been cut closer to and potentially below skin surface 61. It is noted that if it is favourable for the purpose of hair-skin manipulation or if cutting should take place without reaching the skin surface 61, an additional skin stretcher is installable in front of the optical blade 59 in order to stretch the skin, make the skin doming more predictable and ensure that the cutting light remains parallel to and/or above the exposed skin area 61. Preferably, the skin stretcher additionally doubles as a laser beam deflector, whereby the light that reaches the stretcher is deflected upward and/or away from the skin surface 61 and absorbed inside the hair cutting device.

It is noted that the outline of the optical blade does not necessarily coincide with the outline of the mechanical skin interface. If desired, mechanical means, for instance for the support of the optical blade or for skin manipulation, could be added. This makes the blade-skin interface preferably more comfortable and/or pleasant when used at a relatively high skin pressure.

When shaving against the direction of hair growth on the skin, the blade preferably positions the hair in a substantially upright position relative to the blade cross section. Once the base of the hair 69, i.e. the point where the hair 69 enters the skin, comes into contact with the blade 59 it will preferably be dragged along with the blade 59 for a considerable amount of time. Thereby, the skin preferably gradually deforms and builds up sufficient stress to cause the hair to eventually bend underneath the blade. During this time the hair 69 preferably sits conveniently in a detection plane of the optical blade 59, ensuring that sufficient time is available for detection and/or cutting to take place and/or for cutting the hair 69, after which it will slide easily underneath the optical blade 59.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A laser scanning system for scanning a laser beam of a hair cutting device, the laser scanning system comprising:
   a laser scanning device configured to generate a scanning movement of the laser beam;
   a movable optical device configured to at least one of adjust and focus the laser beam,
   wherein the laser scanning device comprises a movable optical element and a fixed optical system,
   wherein the movable optical element is mechanically coupled to the movable optical device such that the movable optical element follows motion of the movable optical device back and forth along a moving axis,
   wherein the movable optical element is arranged to inter-relate a position of the movable optical device to a mobile access-position where the laser beam enters the fixed optical system, and
   wherein the fixed optical system is arranged to inter-relate said mobile access-position to at least one corresponding position where the laser beam is incident on the movable optical device, the at least one corresponding position being at the movable optical device.

2. The laser scanning system according to claim 1, wherein the movable optical element and the movable optical device are fixed to one another.

3. The laser scanning system according to claim 1, wherein the movable optical element is a reflective element adjusted for reflecting the laser beam in a direction parallel to the moving axis of the movable optical element and the movable optical device.

4. The laser scanning system according to claim 3, wherein the reflective element is arranged in a 45° orientation with respect to an incoming direction and with respect to an outgoing direction of the laser beam.

5. The laser scanning system according to claim 1, wherein the movable optical device comprises an array of optical lenses configured to at least one of adjust and focus the laser beam.

6. The laser scanning system according to claim 1, wherein the mobile access-position where the laser beam enters the fixed optical system is a position on a first reflector of the fixed optical system.

7. The laser scanning system according to claim 6, wherein the fixed optical system further comprises a second reflector and a third reflector, and wherein each of the first, second and third reflectors is arranged in a 45° orientation with respect to an incoming direction and with respect of an outgoing direction of the laser beam.

8. The laser scanning system according to claim 7, wherein the movable optical device comprises an array of optical lenses configured to at least one of adjust and focus the laser beam, and wherein at least one of the first, second and third reflectors is part of a faceted prism for selectably addressing of individual optical lenses of the array.

9. The laser scanning system according to claim 1, wherein the fixed optical system further comprises at least one focusing element.

10. A hair-cutting device, comprising:
    a laser scanning system;
    a detection system for detecting hair with a laser detection device; and
    a cutting-laser system with a cutting laser device,
    wherein the laser scanning system comprises:
    a laser scanning device for configured to generate a scanning movement of the laser beam;

a movable optical device configured to at least one of adjust and focus the laser beam, wherein the laser scanning device comprises a movable optical element and a fixed optical system, wherein the movable optical element is mechanically coupled to the movable optical device such that the movable optical element follows motion of the movable optical device back and forth along a moving axis, wherein the movable optical element is arranged to inter-relate a position of the movable optical device to a mobile access-position where the laser beam enters the fixed optical system, and wherein the fixed optical system is arranged to inter-relate said mobile access-position to at least one corresponding position where the laser beam is incident on the movable optical device, the at least one corresponding position being at the movable optical device.

11. The hair-cutting device according to claim 10, wherein at least one of the detection system and the cutting-laser system use a common optical path of the hair-cutting device.

12. The hair-cutting device according to claim 11, wherein the detection system comprises a beam-splitting device arranged in the common optical path, wherein the beam-splitting device is optically connected to the laser detection device by a first optical path and is optically connected to a detection device by a second optical path.

13. The hair-cutting device according to claim 11, wherein the detection device comprises a focusing system, pin hole and a detector arranged in the second optical path.

14. The hair-cutting device according to claim 11, wherein the cutting-laser system comprises a further beam-splitting device arranged in the common optical path, which further beam-splitting device is connected to the cutting laser device by a further optical path.

15. A method of scanning a laser beam comprising acts of:
generating by a laser scanning device a scanning movement of the laser beam;
at least one adjusting and focusing the laser beam by a movable optical device, wherein the laser scanning device comprises a movable optical element and a fixed optical system, wherein the movable optical element is mechanically coupled to the movable optical device such that the movable optical element follows motion of the movable optical device back and forth along a moving axis;

inter-relating by the movable optical element a position of the movable optical device to a mobile access-position where the laser beam enters the fixed optical system; and inter-relating, by the fixed optical system, said access-position of the laser beam to at least one corresponding position on the movable optical device where the laser beam is incident on the movable optical device, the at least one corresponding position being at the movable optical device.

16. The method of claim 15, wherein the act of at least one adjusting and focusing directs the laser beam by the movable optical element in a direction parallel to the moving axis of the movable optical element and the movable optical device.

17. The method of claim 15, wherein the mobile access-position where the laser beam enters the fixed optical system is a position on a first reflector of the fixed optical system.

18. The method of claim 17, wherein the fixed optical system further comprises a second reflector and a third reflector, and wherein each of the first, second and third reflectors is arranged in a 45° orientation with respect to an incoming direction and with respect of an outgoing direction of the laser beam.

19. The method of claim 18, wherein the movable optical device comprises an array of optical lenses configured to at least one of adjust and focus the laser beam, and wherein at least one of the first, second and third reflectors is part of a faceted prism for selectably addressing of individual optical lenses of the array.

* * * * *